United States Patent [19]

Hudson et al.

[11] Patent Number: 5,112,607
[45] Date of Patent: May 12, 1992

[54] POTENTIATION OF IMMUNOTOXIN ACTION BY BREFELDIN A

[75] Inventors: Thomas H. Hudson, Bethesda; Michael A. King, Laurel, both of Md.

[73] Assignee: The United States of America as represented by the Secretary of the Army, Washington, D.C.

[21] Appl. No.: 715,094

[22] Filed: Jun. 5, 1991

[51] Int. Cl.$^5$ .................... A61K 39/39; A61K 39/395
[52] U.S. Cl. ................... 424/85.91; 530/370; 530/371; 530/377; 530/395; 530/403; 530/404; 530/405; 530/406; 530/391.7; 530/388.22; 424/85.5; 424/88; 424/89; 424/92
[58] Field of Search .......... 424/85.91, 88, 92, 89, 424/85.5; 530/371, 377, 395, 370, 389, 390, 391, 403, 404, 405, 406

[56] References Cited

U.S. PATENT DOCUMENTS

| | | | |
|---|---|---|---|
| 4,439,199 | 3/1984 | Amkraut et al. | 530/351 |
| 4,490,362 | 12/1984 | Shionoya et al. | 514/8 |
| 4,582,703 | 4/1986 | Jansen et al. | 530/391 |
| 4,664,911 | 5/1987 | Uhr et al. | 424/85.91 |
| 4,749,566 | 6/1988 | Casellas et al. | 530/405 X |
| 4,911,911 | 3/1990 | Casellas et al. | 530/371 X |
| 4,911,912 | 3/1990 | Casellas et al. | 530/371 X |
| 4,980,457 | 12/1990 | Jansen | 530/403 X |

OTHER PUBLICATIONS

Merck Index, 10th ed., 1983, p. 189.

*Primary Examiner*—Howard E. Schain
*Attorney, Agent, or Firm*—Werten F. W. Bellamy; Anthony T. Lane

[57] ABSTRACT

A method of potentiating immunotoxin action in an immunotoxin/target-cell system in which Brefeldin A is utilized as an immunopotentiator. The Brefeldin A enhances the immunotoxin pathway while blocking or inhibiting the nonspecific pathway, thus being particularly useful in conjunction with immunotoxins made from holotoxins. The Brefeldin A is effective in small, nontoxic concentrations and therefore may be utilized with either in vivo or in vitro systems.

15 Claims, 2 Drawing Sheets

BFA EFFECTS ON RICIN

FIG. 3

POTENTIATION OF IMMUNOTOXIN ACTION BY BREFELDIN A

TECHNICAL FIELD

The present invention relates to immunotoxin conjugates and their use to selectively delete a target population of cells. More particularly, the present invention relates to a novel potentiator which potentiates the specific cytotoxicity of immunotoxins.

BACKGROUND ART

There presently exist a lack of methodology for killing specific or target cells within a population of cells. Current methods for doing this, such as chemotherapy and radiation therapy are not specific. Moreover, the side effects associated with chemotherapy and radiation therapy are problematic. Immunotoxin therapy is presently being developed to increase the specificity of chemical agents.

As a class, immunotoxins are hybrid compounds designed to kill specific cells while leaving non-target cells intact. Immunotoxins are formed by chemically linking a potent cell toxin to an antibody which is directed against a target cell component. The antibody moiety provides the specificity of the compound while the cell toxicity is a function of the toxin component.

The efficacy of the immunotoxin is dependent on the nature of its components. Monoclonal antibodies against determinants found only, or in much greater numbers, on target cells are used because of their superior specificity and ease of obtaining large amounts of material. The toxins used are generally found in nature as hetero-dimers themselves.

Ricin is one of a number of plant proteins which, in minute quantities, exhibits considerable toxicity toward eukaryotic cells. Ricin is composed of two glycoprotein chains covalently linked via a single disulfide bond. The A chain of ricin, having an apparent molecular weight of about 30,000, is responsible for the expression of toxicity, and acts enzymatically upon the 60S ribosomal subunit leading to irreversible abrogation of protein syntheses. Ricin B chain, having an apparent molecular weight of about 32,000, functions as a lectin with specificity for galactose and serves to bind the toxin to the plasma membrane. The B chain binds to surface determinants found on virtually all cells. Apart from the binding activity, the B chain also functions in the delivery of A chains to the cytosol.

Immunotoxins made of holotoxins, i.e., containing both A and B subunits are potent cytocidal agents. However, the presence of the B subunit with its nonspecific binding nature, results in high levels of non-target cell death. Nevertheless, immunotoxins made of A subunits only are not potent cytotoxins, because they lack the delivery function associated with the B subunits.

A number of U.S. patents directed to the field of immunotoxins are known, including U.S. Pat. No. 4,664,911 to Uhr et al which is directed to immunotoxin conjugates employing toxin B chain moieties; and U.S. Pat. No. 4,582,703 to Jansen et al which is directed to cytotoxic medicaments formed from the association of at least one immunotoxin and chloroquin.

U.S. Patents which are directed to, or otherwise discuss, the use of immunopotentiators include U.S. Pat. No. 4,911,912 to Casellas et al and U.S. Pat. No. 4,749,566 to Casellas et al, each of which contain a discussion of immunopotentiators, and U.S. Pat. No. 4,490,362 to Shionoya et al which is directed to an immunopotentiator which comprises the B chain of ricin as an active ingredient.

There exists a need for a potentiator which potentiates the specific cytotoxicity of immunotoxins which are made of holotoxins.

DISCLOSURE OF THE INVENTION

It is accordingly an object of the present invention to provide a method of killing specific cells within a population of cells.

Another object of the present invention is to provide a method of potentiating specific cytotoxicity of immunotoxins.

A further object of the present invention is to provide for a method of potentiating the immunotoxin activity of immunotoxins made from holotoxins.

A still further object of the present invention is to provide for an immunopotentiator which can be utilized either in vitro or in vivo.

According to these and other objects of the present invention which will become apparent as the description thereof is presented below, there is provided by the present invention a method for potentiating the cytotoxicity of toxin A chain containing conjugates effective to selectively delete target cells from a system including population of cells which comprises adding an amount of Brefeldin A effective to potentiate the cytotoxicity of said toxin A chain containing conjugates.

The present invention also provides a method for potentiating the cytotoxicity of toxin A chain and B chain containing conjugates effective to selectively delete target cells from a system including a population of target cells and non-target cells which comprises adding an amount of Brefeldin A effective to potentiate the cytotoxicity of the toxin A chain and block nonspecific binding of the B chain to non-target cells.

BRIEF DESCRIPTION OF DRAWINGS

The present invention will be described with reference to the annexed drawings, which are given by way of non-limiting examples only, in which:

Figure 3:
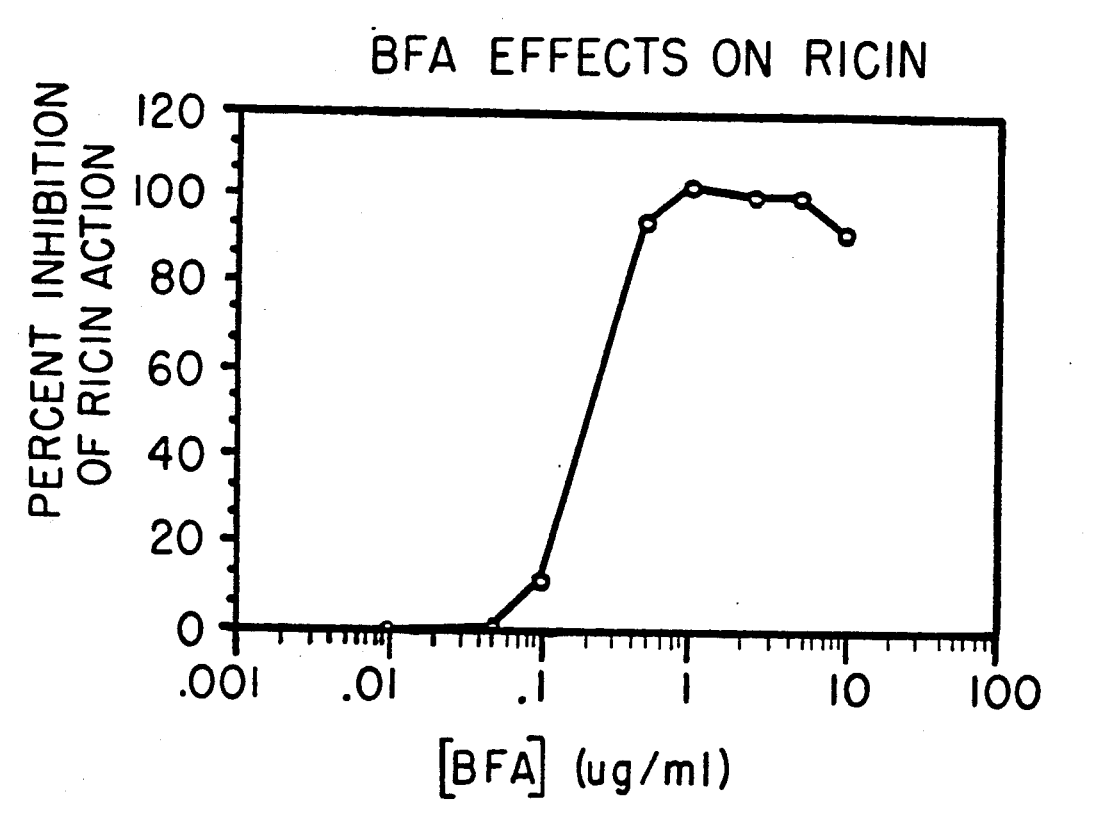

FIG. 3 is a graph illustrating the relationship between percent inhibition of ricin action versus the concentration of BFA.

BEST MODE FOR CARRYING OUT THE INVENTION

Figure 1:
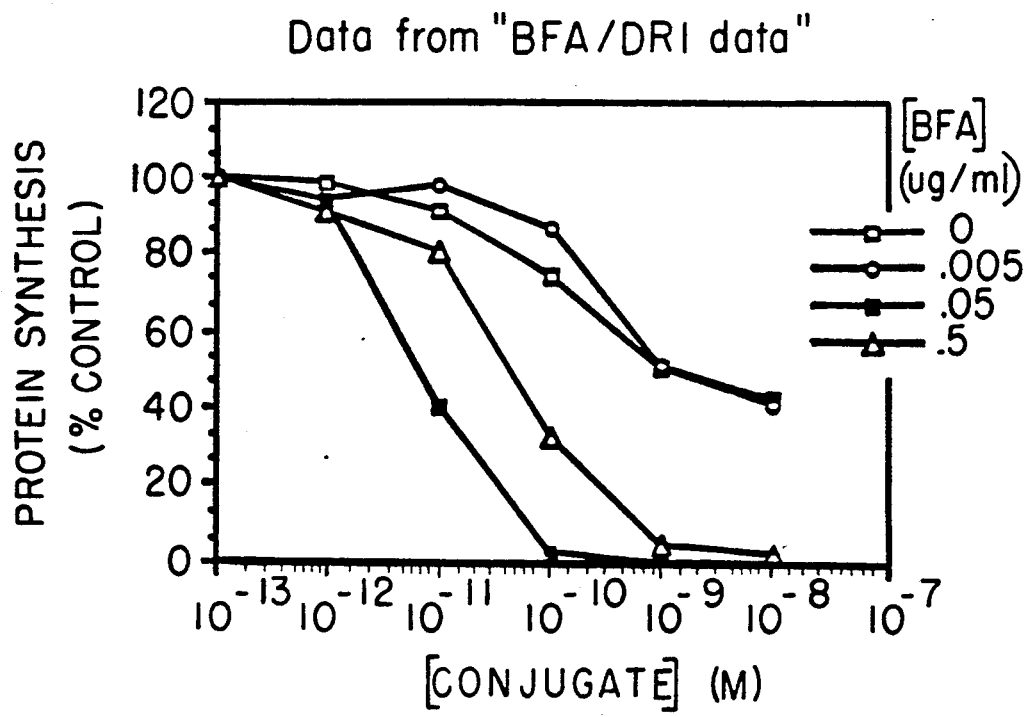
FIG. 1 is a graph illustrating the relationship between the dose/response of the inhibition of protein synthesis versus conjugate concentration in the presence of various concentrations of BFA.
Figure 2:
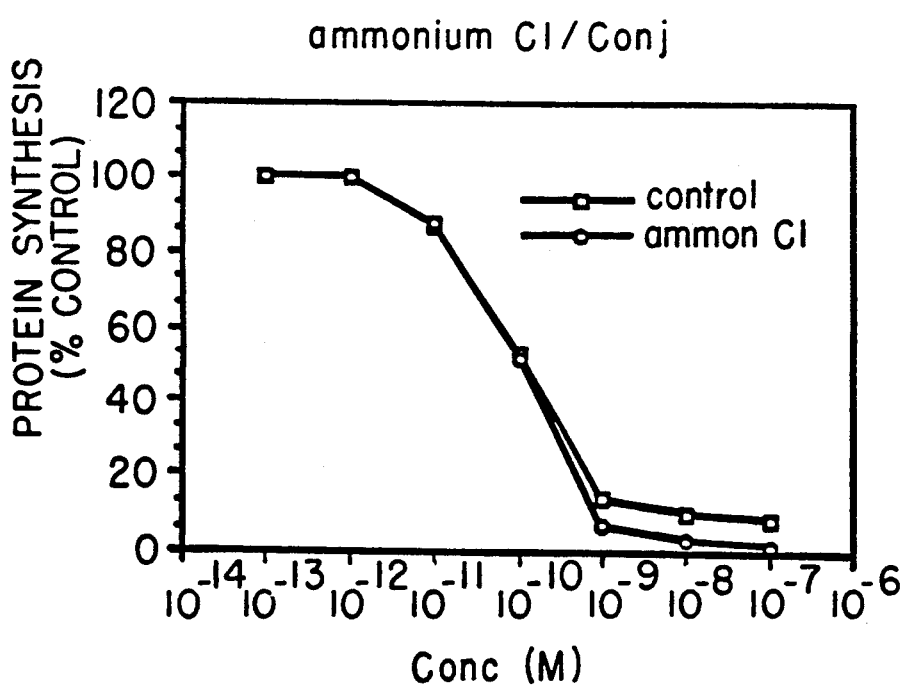
FIG. 2 is a graph illustrating the relationship between the dose/response of the inhibition of protein synthesis versus conjugate concentration in the presence of various concentrations of $NH_4Cl$.

The present invention is directed to a method of potentiating immunotoxins in immunotoxin/target cell systems. More particularly, the present invention is directed to the use of Brefeldin A (BFA) as an immunotoxin potentiator.

According to the present invention, the inventors have discovered that Brefeldin A potentiates a variety of immunotoxins by blocking or inhibiting the nonspecific pathway associated with B subunits, while enhancing the pathway associated with the A subunits. Thus, the presence of BFA produces a dual effect which leads to more effective killing of target cells and reduction of nonspecific killing of non-target cells in a system.

The dual potentiation effect provided by BFA may best be appreciated when utilized in conjunction with immunotoxins made of holotoxins. Thus, the present invention allows for a more effective use of a class of potent cytocidal agents.

In addition to the novel dual potentiation effect provided by BFA, it has been discovered that BFA is effective at concentrations of 0.5 μg/ml or less. This effectiveness at low concentrations and lack of significant side effects associated with the administration of BFA, i.e., low toxicity, is significant in that BFA may be utilized as an immunopotentiator in in vitro or in vivo systems.

According to the present invention BFA may be utilized as a potentiator in conjunction with a variety on immunotoxins, including, but not limited to, diphtheria toxin, modeccin, abrin, Pseudomonas exdotoxin A, ricin, saporin and gelonin.

As indicated above, there are two major modes of immunotoxin therapy currently being developed which can directly benefit from the inventors' discovered use of BFA: in vitro and in vivo. In in vitro treatments, immunotoxins are used clinically to deplete bone marrow explants of T-lymphocytes. This treatment reduces the chances and severity of graft versus host disease when the explants are injected into patients suffering from a number of disease states. This is just one of a series of treatment modes which require the selective elimination of specific cells in vitro. In vivo treatments aimed at specifically reducing the number of undesirable cells, e.g., cancerous cells, within the body are much less developed clinically, but are the aim of a great deal of research. The use of BFA as an effective immunopotentiator according to the present invention at low, nontoxic concentrations allows of both in vitro and in vivo treatments.

The following examples are presented to illustrate the present invention which is not intended to be considered as being limited thereto.

EXAMPLE 1

This example utilized a human lymphoma cell line (ATTCC CRL 8163) derived from the Jurkat cells line. This cell line is widely used as a model cancer cell system. The immunotoxin used in this example (454A12MAB-rRa) was obtained from CETUS Corporation. The immunotoxin consists of the A chain component of ricin toxin covalently linked to a monoclonal antibody directed against the human transferrin receptor. The ricin A chain was produced utilizing recombinant technology.

In this example, the Jurkat cells were suspended in leucine free culture medium and portions of the cell suspension were added to the wells of a multi-well plate containing appropriate test agents including various concentrations of Brefeldin A. After the cell suspension was placed in the wells of the multi-well plate, the plate was immediately placed in a humidified incubator at a temperature of 37° C for 24 hours. After incubation, $^{14}C$ leucine was added for one hour under the same conditions. The cells were harvested and the radioactivity incorporated into the protein was determined and used as an index of cytotoxicity.

FIG. 1 is a graph illustrating the relationship between the dose/response of the inhibition of protein synthesis versus conjugate concentration in the presence of various concentrations of BFA. As can be determined from FIG. 1, the maximum protein synthesis was obtained utilizing a BFA. concentration of 0.05 μg/ml. As indicated in FIG. 1, the $LD_{50}$ of the conjugate is shifted to a concentration over 2.5 logs lower with the BFA. In addition, the population of cells not sensitive to the conjugate (approximately 40%) is eliminated by the presence of the BFA (0.05 and 0.5 μg/ml).

EXAMPLE 2

In this example, potentiation of an immunotoxin utilizing BFA and ammonium chloride ($NH_4Cl$) and monensin are compared for possible use in in vitro and in vivo treatment protocols.

In this example, Jurkat cells were prepared and treated as in Example 1, above. However, various concentrations of $NH_4Cl$ were utilized in place of the Brefeldin A.

FIG. 2 is a graph illustrating the relationship between the dose/response of the inhibition of protein synthesis versus conjugate concentration in the presence of various concentrations of $NH_4Cl$. In FIG. 2, it is seen that $NH_4Cl$ does not significantly alter the dose/response curve of the A subunit immunotoxin. Thus, $NH_4Cl$ is not as effective as BFA for potentiation of immunotoxins.

While both $NH_4Cl$ and monensin have been utilized to potentiate the efficacy of immunotoxins in vitro, $NH_4Cl$ must be present at 10mM to effectively potentiate efficacy; a concentration which is too high for in vivo use. On the other hand, while monensin potentiates in the nM concentration range, it is extremely toxic to the organism and therefore is not usable in either mode of treatment. Moreover, neither $NH_4Cl$ nor monensin potentiate all immunotoxin/target-cell systems.

EXAMPLE 3

In this example Jurkat cells were incubated with $1\times10^{-9}$ M ricin in the presence of various concentrations of BFA for three hours after which the protein synthetic rates were assayed. The results of this example are illustrated in FIG. 3 which shows the relationship between percent inhibition of ricin action versus the concentration of BFA.

As shown in FIG. 3, Brefeldin-A at a concentration of 0.5 μg/ml completely blocks ricin intoxication. This BFA concentration significantly potentiates the A-subunit immunotoxin route. This finding indicates that BFA. may allow the use of holotoxin immunotoxins in a clinical situation because the nonspecific pathway of ricin is blocked or inhibited while the immunotoxin pathway is enhanced. Accordingly, BFA enables the specificity of the holotoxin immunotoxin to be increased while retaining the superior cytotoxicity thereof.

Although the present invention is described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A method for potentiating the cytotoxicity of toxin A chain containing conjugates effective to selectively delete target cells from a system including a population of cells which comprises aiding an amount of Brefeldin A effective to potentiate the cytotoxicity of said toxin A chain containing conjugates.

2. A method for potentiating the cytotoxicity of toxin A chain containing conjugates according to claim 1, wherein said effective amount of Brefeldin A is up to about 0.5 µg/ml.

3. A method for potentiating the cytotoxicity of toxin A chain containing conjugates according to claim 2, wherein said effective amount of Brefeldin A is up to about 0.05 µg/ml.

4. A method for potentiating the cytotoxicity of toxin A chain containing conjugates according to claim 1, wherein said toxin A chain containing conjugates include immunotoxins made from holotoxins.

5. A method for potentiating the cytotoxicity of toxin A chain containing conjugates according to claim 1, wherein said toxin A chain containing conjugates include immunotoxins selected from the group consisting of diphtheria toxin, modeccin, abrin, Pseudomonas exdotoxin A, ricin, saporin, gelonin, and combinations thereof.

6. A method for potentiating the cytotoxicity of toxin A chain containing conjugates according to claim 5, wherein said toxin A chain containing conjugates consists of ricin.

7. A method for potentiating the cytotoxicity of toxin A chain containing conjugates according to claim 1, wherein said system comprises an in vivo system.

8. A method for potentiating the cytotoxicity of toxin A chain containing conjugates according to claim 1, wherein said system comprises an in vitro system.

9. A method for potentiating the cytotoxicity of toxin A chain and B chain containing conjugates effective to selectively delete target cells from a system including a population of target cells and non-target cells which comprises adding an amount of Brefeldin A effective to potentiate the cytotoxicity of the toxin A chain and inhibit nonspecific binding of the B chain to non-target cells.

10. A method for potentiating the cytotoxicity of toxin A chain and B chain containing conjugates according to claim 9, wherein said effective amount of Brefeldin A is up to about 0.5 µg/ml.

11. A method for potentiating the cytotoxicity of toxin A chain and B chain containing conjugates according to claim 10, wherein said effective amount of Brefeldin A is up to about 0.05 µg/ml.

12. A method for potentiating the cytotoxicity of toxin A chain and B chain containing conjugates according to claim 9, wherein said toxin A chain and B chain containing conjugates include immunotoxins selected from the group consisting of diphtheria toxin, modeccin, abrin, Pseudomonas exdotoxin A, ricin, saporin, gelonin, and combinations thereof.

13. A method for potentiating the cytotoxicity of toxin A chain and B chain containing conjugates according to claim 12, wherein said toxin A chain and B chain containing conjugates consists of ricin.

14. A method for potentiating the cytotoxicity of toxin A chain and B chain containing conjugates according to claim 9, wherein said system comprises an in vivo system.

15. A method for potentiating the cytotoxicity of toxin A chain and B chain containing conjugates according to claim 9, wherein said system comprises an in vitro system.

* * * * *